United States Patent [19]

Ripka

[11] 4,042,707

[45] Aug. 16, 1977

[54] 3α-ARYLHYDROISOINDOLES

[75] Inventor: William Charles Ripka, Wilmington, Del.

[73] Assignee: E. I. Du Pont de Nemours and Company, Wilmington, Del.

[21] Appl. No.: 659,510

[22] Filed: Feb. 19, 1976

[51] Int. Cl.$^2$ .................... A61K 31/40; C07D 209/44
[52] U.S. Cl. ................................ 424/274; 260/326 R; 260/326.1; 260/326.44; 260/346.3; 260/465 D; 260/465 F; 260/473 R; 260/515 R; 260/570.5 R; 260/570.6
[58] Field of Search ....................... 260/326.1; 424/274

[56] References Cited

U.S. PATENT DOCUMENTS

| 3,031,459 | 4/1962 | Huebner .......................... 260/326 R |
| 4,001,248 | 1/1977 | Zimmerman et al. ......... 260/326.1 X |

FOREIGN PATENT DOCUMENTS 898,590  6/1962  United Kingdom .............. 260/319.1

OTHER PUBLICATIONS

Gschwend et al., "J. Org. Chem.," vol. 41, pp. 104–110, (1976).
Armarego et al., "J. Chem. Soc.," vol. 19(c), pp. 3222–3229, (1971).
Kugita, "Chem. Abstracts," vol. 51, pp. 1992d–1993f, (1957).

*Primary Examiner*—Ethel G. Love
*Attorney, Agent, or Firm*—Anthony P. Mentis

[57] ABSTRACT

Certain 3α-arylhydroisoindoles are useful as analgesics and/or narcotic antagonists. Exemplary is N-cyclopropylmethyl-3α-(m-methoxyphenyl)-5,6-dimethyl-2,3,3α,4,7,7α-trans-hexahydroisoindole.

63 Claims, No Drawings

3α-ARYLHYDROISOINDOLES

BACKGROUND OF THE INVENTION

1. Field of the Invention

The invention relates to certain 3a-arylhydroisoindoles useful as analgesics. Some are additionally useful as narcotic antagonists.

2. Prior Art

British Pat. No. 898,590 published June 14, 1962 describes octahydroindoles useful as tranquilizers. These compounds have a different method of synthesis and different pharmacological properties from the isoindoles of this invention. They also have different structures; and although this patent refers to "iso" it refers to isomeric indoles (cis, trans) rather than to the isoindole structure.

DESCRIPTION OF THE INVENTION

This invention is a compound of the group (A) having the general formula

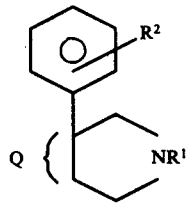

I wherein $R^1$ is hydrogen, alkyl of 1 to 8 carbons,

—$CH_2Y$ where Y is alkenyl or alkynyl of 2-6 carbons,

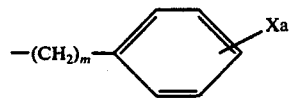

where $m$ is 1 or 2, $a$ is 0 or 1 and X is F, Cl, Br, $CF_3$, $OCH_3$, $CH_3$, $C_2H_5$, $C_3H_7$, $C_4H_9$, $NH_2$ or $N(CH_3)_2$,

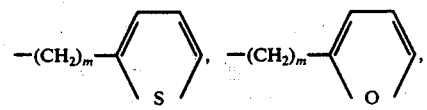

or cycloalkylmethyl of the formula

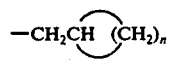

where $m$ is 1 or 2 and $n$ is 2–5;

$R^2$ is H, OH, $OCH_3$, F, or

where $R^3$ is alkyl of 1–3 carbons; and

Q is:

(1)

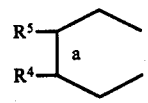

in which $R^4$ and $R^5$ are each H or $CH_3$; or $R^4$ and $R^5$ are H, $CH_3$, $C_2H_5$, $i$-$C_3H_7$, Cl, or $OCH_3$ with the proviso that one only of $R^4$ or $R^5$ is hydrogen;

$a$ is a single or double bond; with the proviso that when $R^4$ or $R^5$ is Cl or $OCH_3$, $a$ is a double bond; or (2)

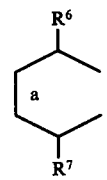

in which $R^6$ and $R^7$ are each OH or $OCOCH_3$; or $R^6$ and $R^7$ are H, OH, $OCOCH_3$, $OCH_3$ or $CH_3$ with the proviso that one only of $R^6$ or $R^7$ is H;

$a$ is a single or double bond; or (3)

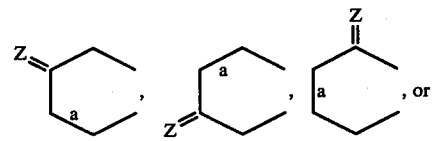

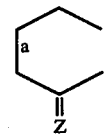

in which

Z is O or

and $a$ is a single or double bond; and (B) a pharmaceutically acceptable acid addition salt of (A).

The pharmaceutically acceptable acid addition salts include the hydrochloride, sulfate, phosphate, nitrate, citrate, tartrate, maleate, and the like.

The compound of the invention have unexpected beneficial utility in being useful as analgesic agents in mammals. Some of the compounds also have narcotic antagonist activity. The invention therefore includes a pharmaceutical composition comprising a suitable pharmaceutical carrier and a compound of the invention. It also includes a method of producing analgesia or narcotic atagonism in a mammal which comprises administering to the mammal an effective analgesic or narcotic antagonistic amount of a compound of the invention.

The numbering system used is as follows:

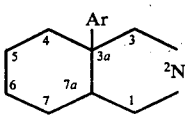

When position 7a possesses a hydrogen atom the molecule may exist in a cis- or trans- form.

Two general methods are available for the synthesis of the compounds. In the first general method an α-aryl-maleic anhydride (1) or an α-aryl-maleimide (5) is reacted with a diene to yield the corresponding cis-anhydride or imide. The resultant cis-1-aryl-4-cyclohexene-1,2-dicarboxylic acid anhydride (3) is then reacted with an amine to obtain an alkylated cis-imide (4) (Process A-1). Alternatively the cis-1-aryl-4-cyclohexene-1,2-dicarboximide (6) can be alkylated with sodium amide and an alkylating agent (Process A-2) leading to the same alkylated cis-imide (4) as in A-1. The Ar group in the reactions below indicate a phenyl group, a methoxyphenyl group or a fluorophenyl group.

A-1

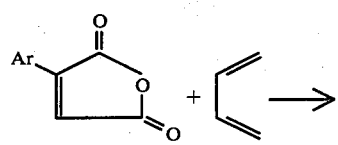

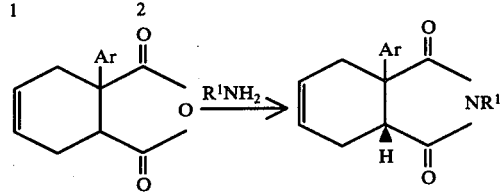

A-2

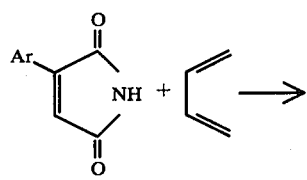

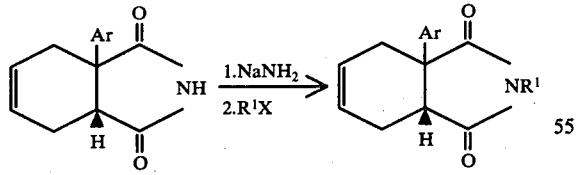

The alkylating agent can be $R^1X'$ where $X'$ is iodine or bromine and $R^1$ is as previously stated except that it is not hydrogen. The alkylating agent can also be a tosylate

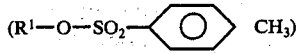

or a mesylate ($R^1$- O SO$_2$CH$_3$) where $R^1$ is as previously stated except it is not hydrogen.

α-(m-Methoxyphenyl)maleimide (5) and anhydride (1) can also be prepared by the following reaction scheme:

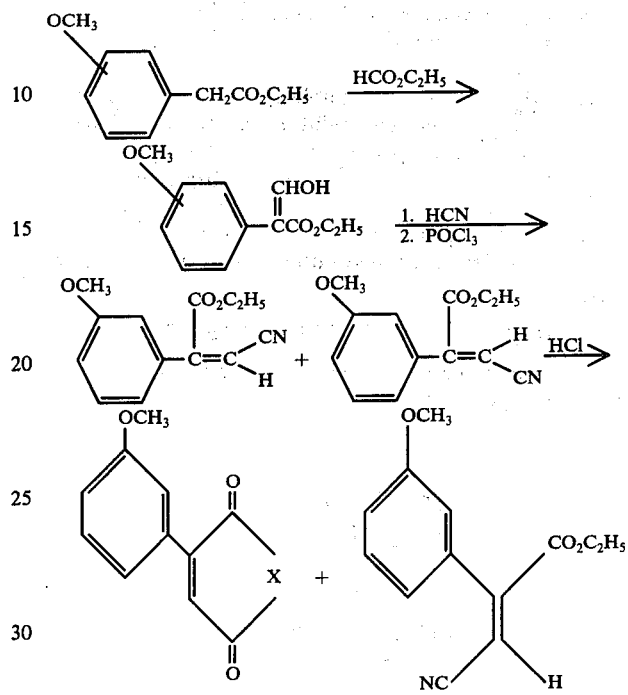

X = NH or O

The product imide (4) from A-1 or A-2 can be reduced with hydrogen and a suitable catalyst such as palladium on carbon, followed by reduction of the imide carbonyl with lithium aluminum hydride (LAH) to form a cis-3a-aryloctahydroisoindole (I) (Process B-1).

B-1

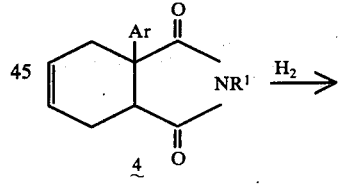

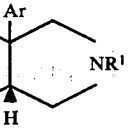

I

If $R^1$ contains unsaturation such that it would be reduced in the hydrogenation step of B-1 an alternate course (Process B-2) is taken, i.e., the hydrogenation is carried out before the alkylation.

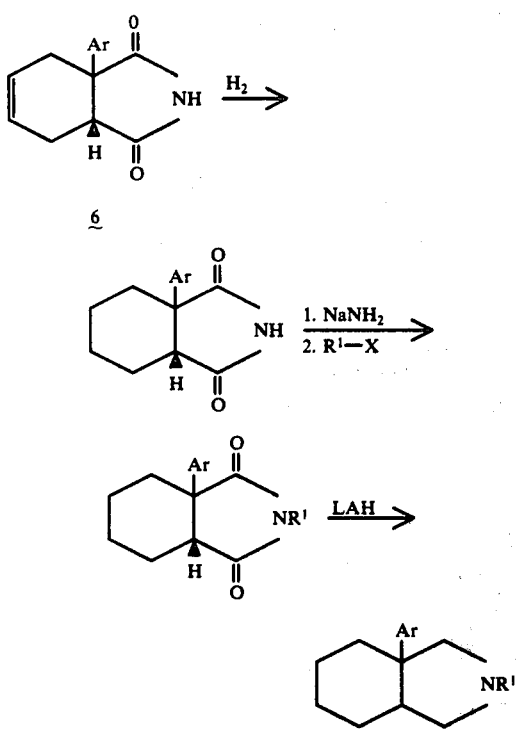

Process B-3 can be used to obtain the desired products regardless of unsaturation present in R¹.

Although processes A-1 and A-2 illustrate 1,3-butadiene as the diene component, any 1,3-diene can be used, as for example those shown below.

The second general method for making the compounds of the invention is provided by the following sequence (c-1). Ethyl benzoyl- or ethyl m-methoxybenzoylacetate is prepared by the general procedure of Straley et al., Organic Synthesis, Col Vol IV, Wiley, N.Y., 1963, page 415, and is converted by hydrocyanation and dehydration to ethyl $\beta$-(m-methoxyphenyl)-$\beta$-cyano-propenoate (9). This material is reacted with a diene to give a 4-aryl-4-cyano-5-carbethoxy cyclohexene (10) which is reduced with a metal hydride such as lithium aluminum hydride (LAH) to the corresponding amino alcohol (11).

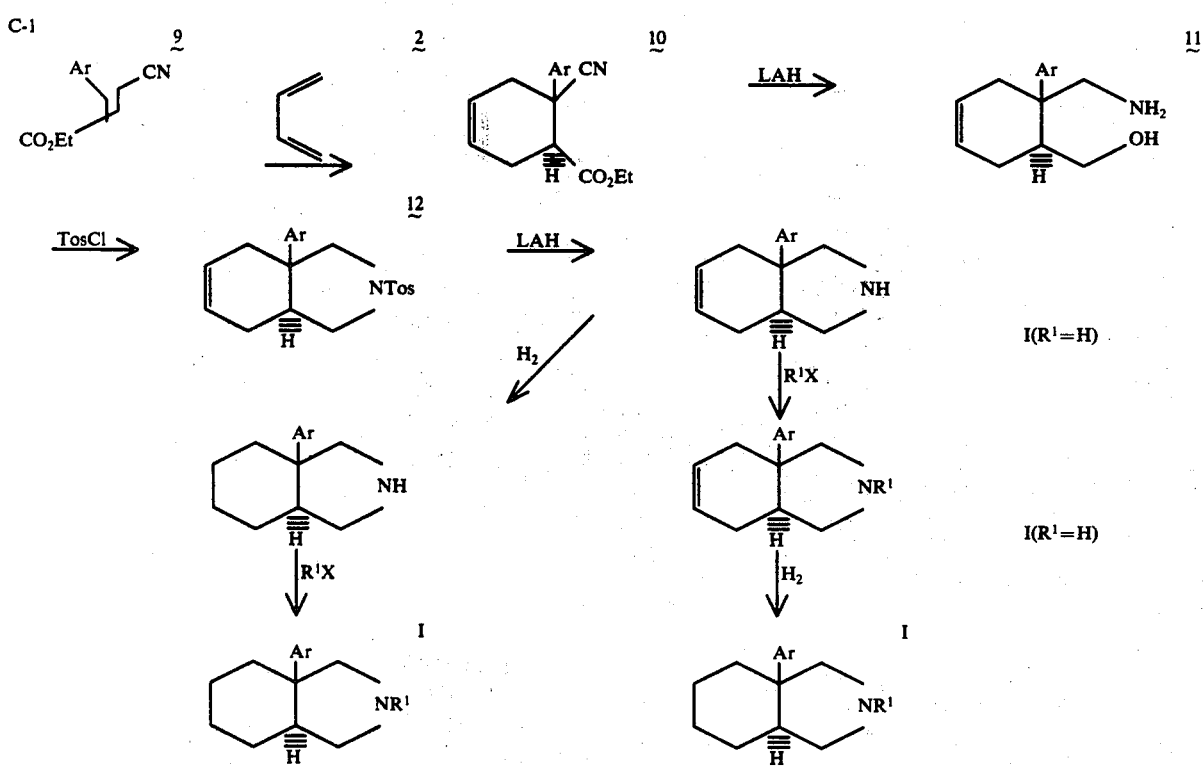

The amino alcohol is reacted with a sulfonyl chloride such as p-toluenesulfonyl chloride to yield the N-tosyl-3a-arylhexahydroisoindole (12). The tosyl group is removed with lithium aluminum hydride, then the compound is either alkylated directly or, if the R¹ group contains reducible functionality, it is reduced to the 3a-aryloctahydroisoindole which can then be alkylated.

Alkylation of a product produced in B-3 can also be achieved by acylation with an appropriate acylating agent, which when reduced, gives the corresponding R¹ compound. For example:

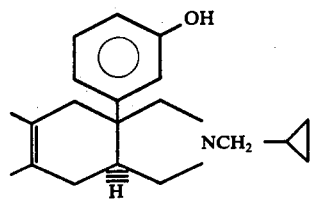

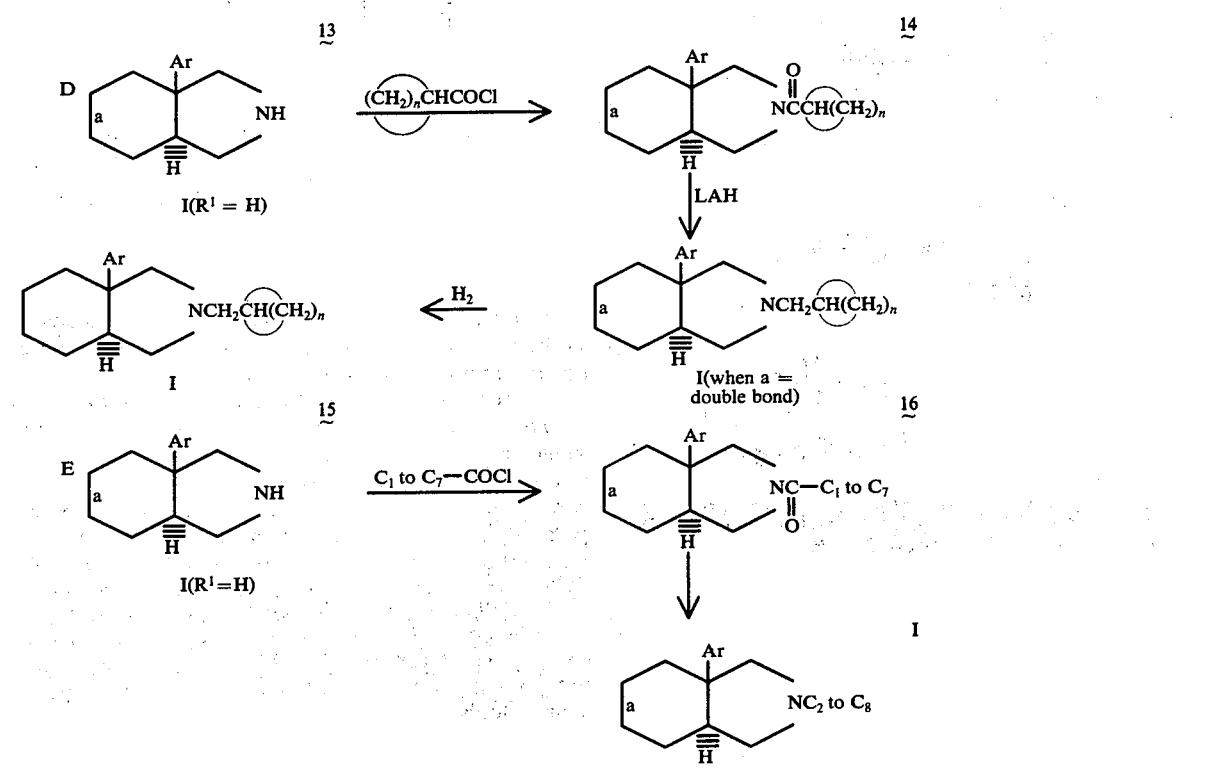

The corresponding esters may be obtained from the hydroxy compounds by conventional esterification procedures.

By the procedures described above all of the compounds embraced by the general formula I can be prepared.

The isoindoles which do not possess a double bond at 7,7a-position may exist in cis or trans forms. The processes A-1 and A-2 lead to cis fused rings resulting in cis-3a-aryloctahydroisoindoles and the processes of C-1 lead to predominantly trans compounds as a result of the structure of the ethyl β-aryl-β-cyanopropenoate, as in reaction scheme F.

Alternatively,

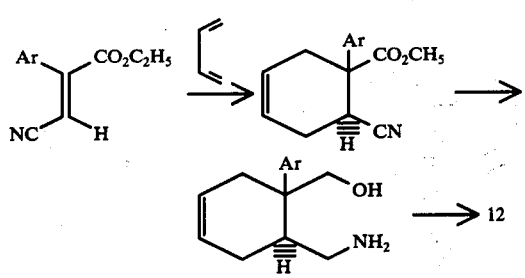

The 3a-m-hydroxyphenyl compounds are prepared by reaction of the 3a-m-methoxyphenyl compounds with pyridine-hydrochloride, as for example,

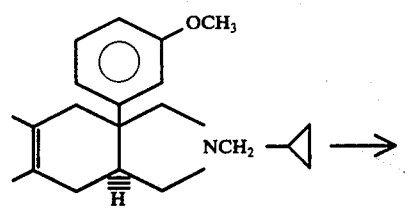

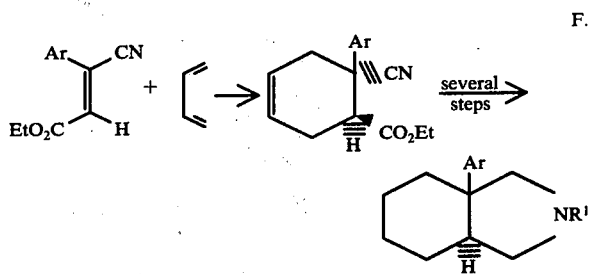

These compounds may also exist as optical isomers, which are separable into optical antipodes by known procedures.

Miller et al., *J. Am. Chem. Soc.*, 72, 1484 (1950) have shown that Diels-Alder adducts are obtained with α-phenylmaleic anhydride and 2,3-dimethylbutadiene, 1,3-butadiene, isoprene, 2-ethyl-1,3-butadiene, and 2-isopropyl-1,3-butadiene. These respectively would give the following products (after formation of imide and reduction with lithium aluminum hydride):

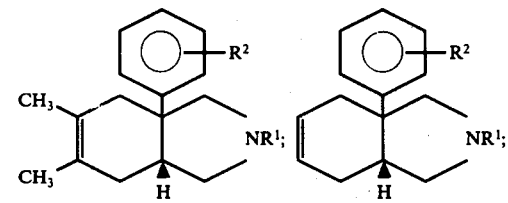

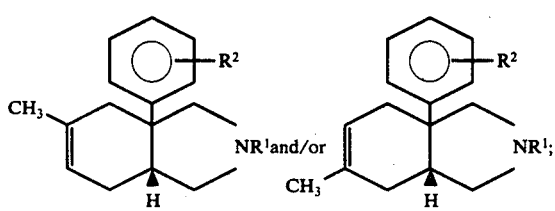

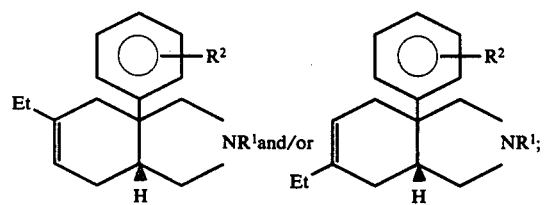

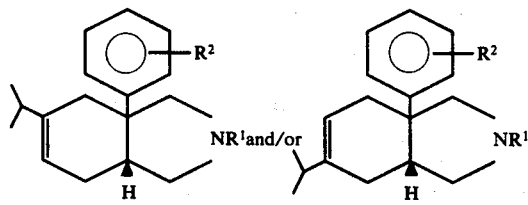

1,4-Diacetoxybutadiene has been shown to give Diels-Alder adducts [Hill et al, Tetrahedron Letters 1157, 1964 and J. Org. Chem. 30, 241F (1965)]. This results in the following product (after reacetylation after lithium aluminum hydride reduction wich would cleave the acetates to hydroxyls):

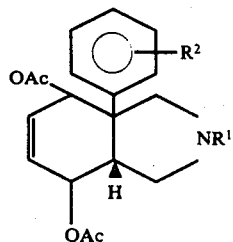

trans-1-Methoxy-3-trimethylsilyloxy-1,3-butadiene [Danishefsky et al., J. Am. Chem. Soc., 96 7807 (1974)] gives the products,

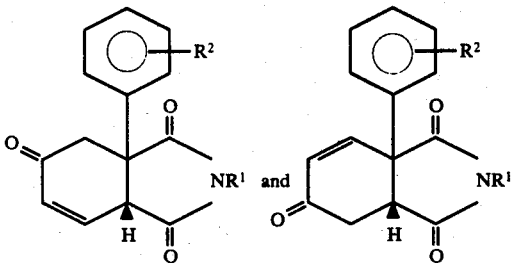

which after LAH reduction of all carbonyls and reoxidation of the resulting allylic alcohol gives,

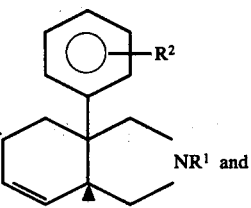

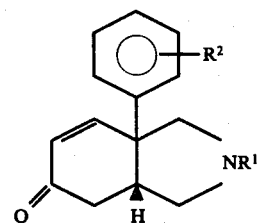

Fieser et al. (Reagents for Organic Synthesis, Wiley, N.Y. 1967, Pages 8, 182) lists other dienes reactive towards maleic anhydride. The α-aryl maleic anhydrides when reacted with dienes such as 1-methoxy-1,3-butadiene, 1-methyl-1,3-butadiene, 2-chloro-1,3butadiene and 1-acetoxy-1,3-butadiene respectively lead to the following products:

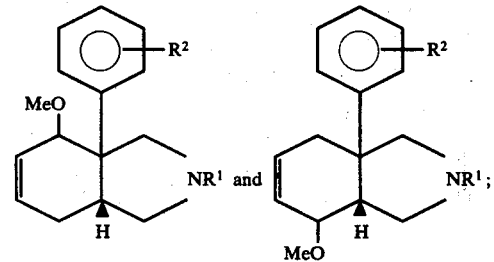

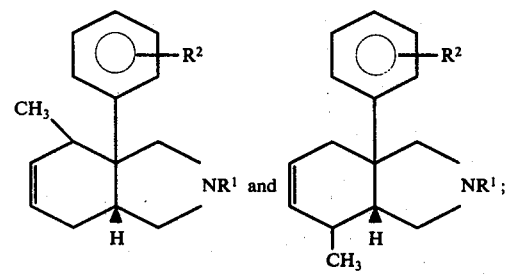

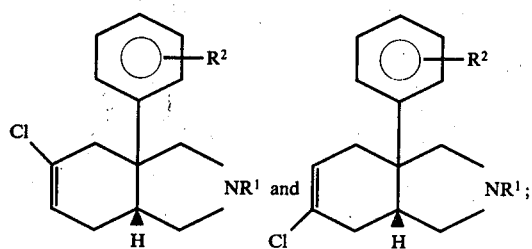

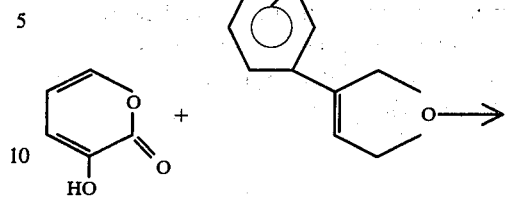

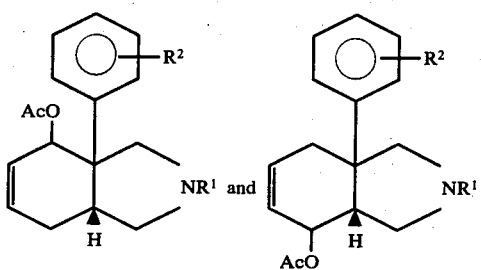

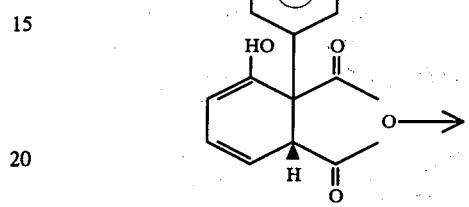

2-Methoxy-1,3-butadiene is also available and will react as follows:

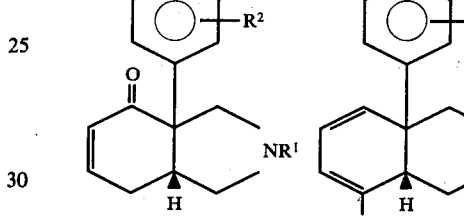

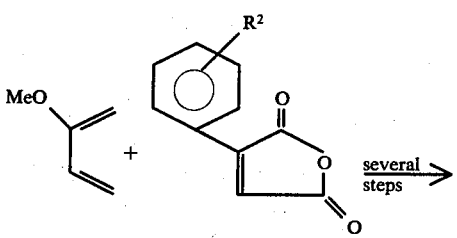

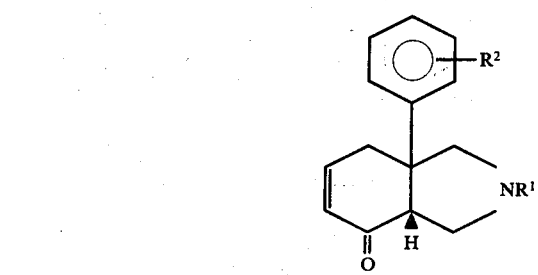

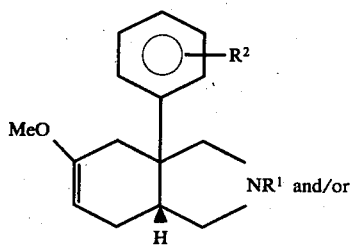

Finally, E. J. Corey [Tetrahedron Letters, 2389 (1975)] has described 3-hydroxy-2-pyrone as a useful diene in Diels-Alder syntheses:

These dienes, among others, can also be reacted with a compound such as ethyl-β-(m-methoxyphenyl)-β-cyanopropenoate (see structured formula 9) to prepare the compounds of the invention having a trans configuration, as indicated by the following:

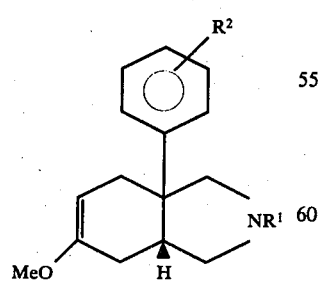

When the R^4-7 groups are alkyl or methoxy the reactions outlined will give the corresponding products directly. For those dienes which have acetoxy, or result in carbonyls after the addition, modification (such as protection or reoxidation, etc.) is necessary to give the products indicated.

SPECIFIC EMBODIMENTS OF THE INVENTION

In the following illustrative examples of the invention all parts are by weight and all temperatures are Centigrade unless otherwise stated.

EXAMPLE 1

N-Cyclopropylmethyl-3a-(m-methoxyphenyl)-5,6-dimethyl-2,3,3a,4,7,7a-hexahydroisoindole A. Ethyl Benzoyl- and m-methoxybenzoylacetate

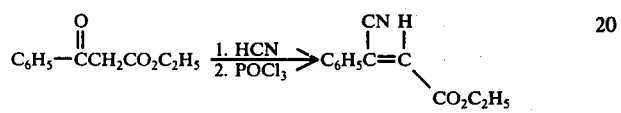

A solution of ethyl benzoylacetate (50 g), 200 ml of hydrogen cyanide and 12 drops of aqueous potassium cyanide was stirred for 24 hrs at 0° C. The reaction was quenched with 12 drops concentrated sulfuric acid and the excess hydrogen cyanide was evaporated. The residue was taken up in 1 N sulfuric acid and extracted with ether. The organic extracts were dried ($MgSO_4$) and evaporated. The resulting oil was taken up in 500 ml of dry pyridine and 50 ml of phosphorous oxychloride was added. The reaction was heated at reflux for 24 hrs, then concentrated, diluted with 3 N hydrochloric acid and extracted with ether. After evaporation of the ether, short-path distillation gave 20 g, bp 115°-120° (.05 mm).

In an analogous way ethyl m-methoxybenzoylacetate, prepared by the general procedure of Straley, et al., Organic Syntheses, Col Vol IV. Wiley 1963 p, 415, with bp 135°-145° (0.5 mm), was reacted as above to yield ethyl β-(m-methoxyphenyl)-β-cyanopropenoate, bp 130° (.01 mm). The product of dehydration is believed to be predominantly the trans isomer A shown below. In support of this, only a single vinyl proton is observed in the nmr spectrum (cf Example 6, Part B) and this occurs at a chemical shift of 6.88δ. Using the method of Matters et al., Tetrahedron, 25, 691 (1969) which estimates the chemical shifts of olefinic protons using additive increments, the chemical shift of the vinyl proton of isomer A is estimated at 6.87δ whereas the vinyl proton of the other possible isomer, B,

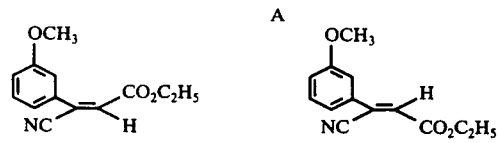

is estimated to be 6.77δ. In addition, hydrolysis of the product with hydrochloric acid gives a diester and not an imide as would be expected in the case where the cyano and ester groups were cis to each other as in isomer B (see Example 6, Part C). There is a single vinyl proton resonance in the nmr spectrum of the diester again indicating this to be a single isomer.

B. 1,2-Dimethyl-4-(m-methoxyphenyl)-4-cyano-5-carbethoxycyclohexene

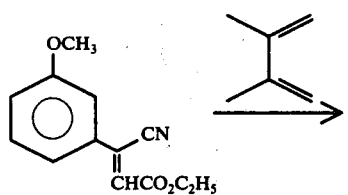

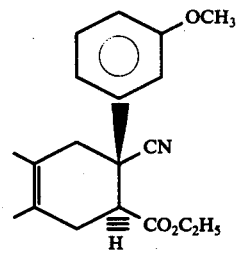

To the product of Part A above (12 g, 51 mmoles) was added 50 ml of 2,3-dimethylbutadiene and 100 of toluene and the solution was refluxed for 48 hrs. Solvent and excess dimethylbutadiene were evaporated and the residue was distilled through a short-path still to yield 9 g, bp 145° (.05 mm).

NMR: triplet at 52,60,67 cps ($CH_2CH_3$, 3H); broad singlet at 102 cps ($CH_3$'s,6H); multiplets at 140-200 cps ($CH_2$'s, CH,5H); singlet at 229 cps ($OCH_3$, 3H); quartet at 228, 234, 241, 248 cps ($OCH_2CH_3$, 2H); multiplets at 400-450 cps (ArH,4H).

IR: 4.45μ (C≡N); 5.75μ ($CO_2Et$); 6.25, 6.35μ (C=C,Ar).

C. 1-(m-Methoxyphenyl)-1-(aminomethyl)-3,4-dimethyl-6-(hydroxymethyl)-2-cyclohexene

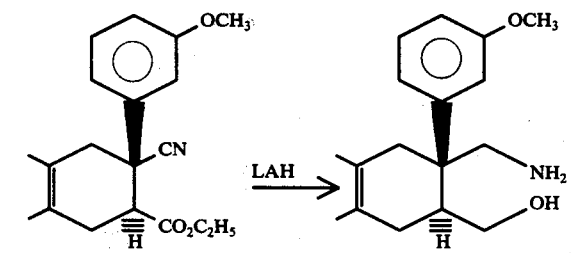

The product from Part B (8 g, 25.5 mmoles) in 200 ml of anhydrous tetrahydrofuran was treated with 8 g of lithium aluminum hydride and the mixture refluxed for 18 hrs. It was quenched with 8 ml of water, 8 ml of 15% sodium hydroxide and 24 ml of water. The inorganic salts were filtered and the filtrate evaporated. The residual crude product, 8.9 g, was used directly in the next step without further purification.

IR: 3.20μ (OH); 3.0μ (NH); 6.25, 6.30μ (Ar).

D. N-(p-Toluenesulfonyl)-3a-(m-methoxyphenyl)-5,6-dimethyl-2,3,3a,4,7,7a-trans-hexahydroisoindole

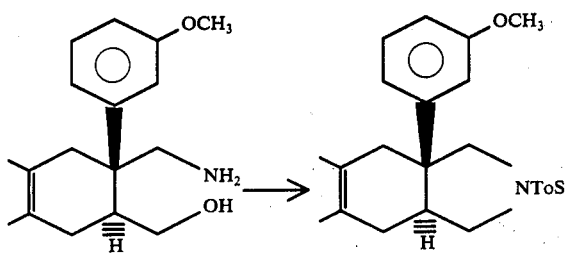

The product from Part C (8.9 g, 32 mmoles) in a solution of 21.1 g triethylamine and 150 ml of anhydrous tetrahydrofuran was treated with 13.8 g of p-toluenesulfonyl chloride and the mixture stirred at 25° for 18 hrs. It was then heated to reflux for 2 hrs, cooled, poured into water and extracted with ether. Evaporation of the ether extracts gave a residue which was evaporatively distilled to yield 6 g, bp 240° (at 5μ).

Anal. Calcd for $C_{24}H_{29}NSO_3$: C, 70.05; H, 7.10; N, 3.40. Found: C, 70.07; H, 7.31; N, 3.39.

HRMS: Calcd for $C_{24}H_{29}NSO_3$: 411.1867. Found: 411,1863.

NMR: multiplet at 58, 65, 72 cps

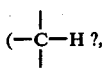

1H); singlet at 90 cps (CH$_3$'s,6H); broad multiplet at 100–130 cps (=CCH$_2$, 4H); singlet at 144 cps (ArCH$_3$, 3H) multiplets at 175–215 cps and singlet at 207 cps (—CH$_2$—N, 4H); singlet at 222 cps (OCH$_3$, 3H); multiplets from 390–470 cps (ArH,8H).

IR: 6.23, 6.30μ (Ar,C=C); 7.50, 8.60μ (SO$_2$N—).

E. 3a-(m-Methoxyphenyl)-5,6-dimethyl-2,3,3a,4,7,7a-trans-hexahydroisoindole

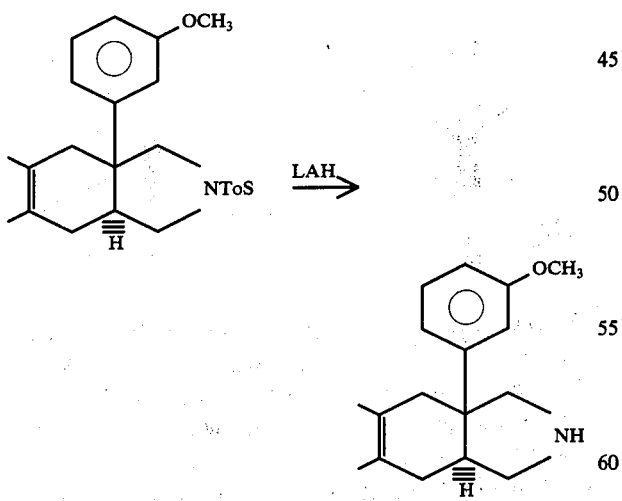

To the product of Part D (6 g, 14.5 mmoles) in 150 ml of anhydrous tetrahydrofuran was added 6 g of lithium aluminum hydride and the mixture was stirred and refluxed under nitrogen for 24 hrs. It was then cooled and quenched with 6 ml of water, 6 ml of 15% sodium hydroxide and finally 18 ml of water. The inorganic salts were filtered and the filtrate evaporated. Evaporative distillation of the residual oil gave 1.5 g, bp 160° (1μ).

HRMS: Calcd for $C_{17}H_{23}NO$: 257.1778. Found: 257.1752.

NMR: broad singlet at 99 cps (CH$_3$'s,6H); multiplets at 115–203 cps (CH$_2$'s and NH,10H); singlet at 228 cps (OCH$_3$3H); multiplets at 400–450 cps (ArH,4H).

IR: 3.0μ (NH); 6.25, 6.35μ (C=C,Ar); bands at 7.5, 8.5μ gone.

F. N-Cyclopropylcarbonyl-3a-(m-methoxyphenyl)-5,6-dimethyl-2,3,3a,4,7,7a-trans-hexahydroisoindole

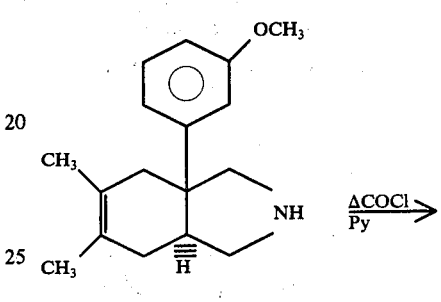

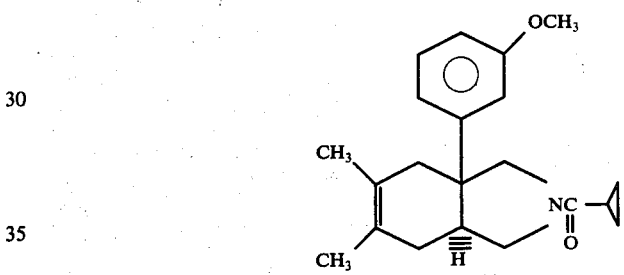

The product from Part E (1.24 g, 4.82 mmoles), anhydrous pyridine (761 mg, 9.63 mmoles) and 25 ml of chloroform was cooled to 0°. Cyclopropylcarbonyl chloride (501 mg, 4.82 mmoles) was added and the reaction mixture stirred at 0°, then at 25° for 18 hrs. The reaction mixture was diluted with water and extracted with ether. The organic extracts were washed with water, 1N hydrochloric acid and brine; then dried with MgSO$_4$ and evaporated to yield 1.33 g. This crude material was chromatographed on 60 g of Silicar CC-7 and eluted with 6% ether-94% benzene to yield 1.1 g of material. Silicar CC-7 is a commercial product based on silica gel and useful for various chromatographic applications.

NMR: Multiplets at 35–76 cps

4H); broad singlet at 99 cps (CH$_3$'s,6H); multiplets at 115–228 cps (CH$_2$'s, 9H); singlet at 229 cps (OCH$_3$, 3H); multiplets at 400–445 (ArH, 4H).

IR: 6.05μ (C=O); 6.25, 6.35μ (C=C,Ar).

G. N-Cyclopropylmethyl-3a-(m-methoxyphenyl)-5,6-dimethyl-2,3,3a,4,7,7a-trans-hexahydroisoindole

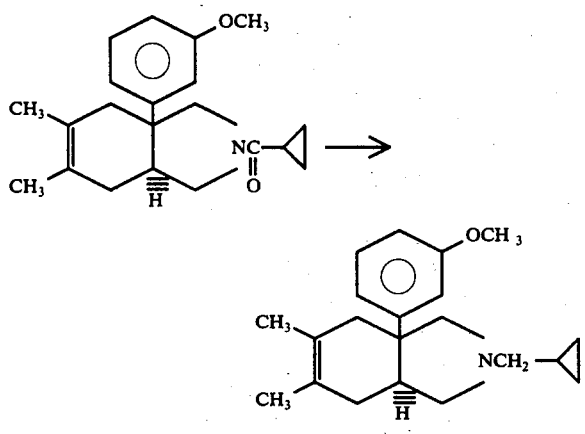

The product from Part F (1.05 g, 3.2 mmoles) together with 75 ml of anhydrous tetrahydrofuran and 1.1 g (29 mmoles) of lithium aluminum hydride were refluxed for 18 hrs. The reaction was quenched with 1.1 ml of water, 1.1 ml of 15% sodium hydroxide solution and finally with 3.3 ml of water. The inorganic salts were filtered and the filtrate evaporated to yield 970 mg of crude product which was evaporatively distilled, bp 140° (0.07 mm).

Anal. calcd for $C_{21}H_{29}NO$: C, 80.98; H, 9.39; N, 4.50. Found: C, 80.54; H, 9.56; N, 5.17.

HRMS: Calcd for $C_{21}H_{29}NO$: 311.2248. Found: 311.2239.

NMR: multiplets at 0–50 cps ( ,

5H); broad singlet at 100 cps (CH$_2$'s,6H), multiplets at 110 to 200 cps (CH$_2$'s,11H); singlet at 228 cps (OCH$_3$, 3H); multiplets at 395–440 cps (ArH,4H).

EXAMPLE 2

N-Cyclopropylmethyl-3a-(m-hydroxyphenyl)-5,6-dimethyl-2, 3,3a,4,7,7a-trans-hexahydroisoindole

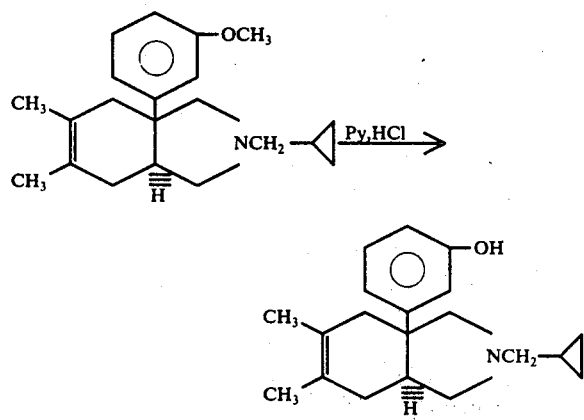

The product from Example 1 Part G (330 mg, 1.06 mmoles) and pyridine hydrochloride (1.2 g, 10.4 mmoles) were heated under nitrogen at 200° C for 1 hr. The reaction was then cooled, diluted with water and treated with solid potassium carbonate until the mixture was strongly basic to pH paper. Extraction with methylene chloride yielded 200 mg of a dark oil which was evaporatively distilled, bp 200° (2μ).

HRMS: Calcd for $C_{20}H_{27}NO$: 297.2091. Found: 297.2075.

IR: Brod Peak from 3–4μ (OH); 6.25, 6.35μ (C=C,Ar).

EXAMPLE 3

N-Allyl-3a-phenyl-2,3,3a,4,7,7a-hexahydroisoindole

A. 1-Phenyl-4-cyclohexene-1,2-dicarboxylic Acid Anhydride

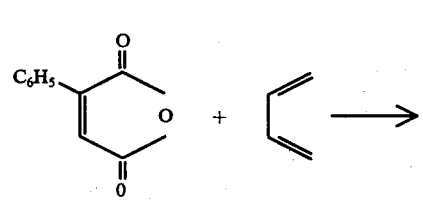

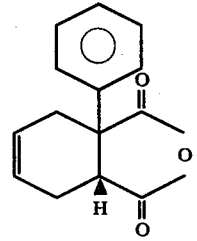

A mixture of α-phenyl-maleic anhydride (20 g, 0.115 moles), butadiene (40 g, 0.74 moles) and 200 ml of toluene was heated at 100° C in a sealed bomb for 15 hrs. The toluene solution was decanted from an insoluble, polymeric material and evaporated in vacuo to yield crude 1-phenyl-4-cyclohexene-1,2-dicarboxylic acid anhydride, bp 155° (0.3 mm).

NMR: multiplets from 130 to 185 cps (CH$_2$'s,4H); set of doublets at 207,210 and 215,217 cps

1H); multiplets at 355 to 365 cps (=CH,2H); singlet at 442 cps (ArH,5H).

B. N-Allyl-1-phenyl-4-cyclohexene-1,2-dicarboximide

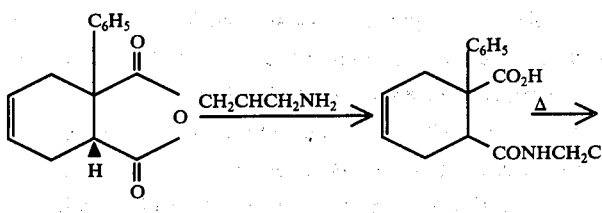

Allylamine (4 g, 0.07 mole) was added to the first product from Part A (5.2 g, .022 moles) and 25 ml of benzene and the solution refluxed for 90 min. then allowed to stand at 25° C for 18 hrs. The reaction was concentrated in vacuo, then taken up in water and extracted with ether. The aqueous layer was acidified with 2N hydrochloric acid to yield 4.2 g of the intermediate amidic acid, mp 130.5°–132.5°.

The solid amidic acid was heated under nitrogen at 190°–200° for 1 hr to yield 2.47 g of an oil identified as the N-allyl-1-phenyl-4-cyclohexene-1,2-dicarboximide.

NMR: multiplets from 130–190 cps (=CCH$_2$,4H); AB quartet at 193,196 and 200, 203 cps

1H); doublet (further split) at 244, 250 cps (NCH$_2$—CH,2H); complex multiplets at 297 to 363 cps (CH=CH and CH=CH$_2$,5H); singlet at 441 cps (ArH,5H).

C. N-allyl-3a-phenyl-2,3,3a,4,7,7a-cis-hexahydroisoindole

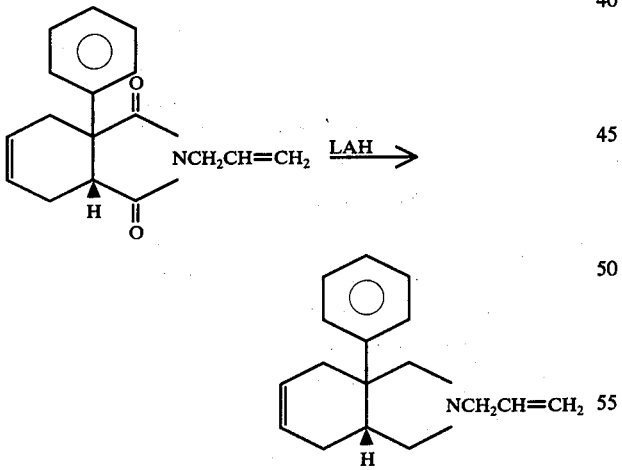

A mixture of the product from Part B (2.37 g), lithium aluminum hydride (2.4 g) and anhydrous tetrahydrofuran (50 ml) was refluxed for 18 hrs under nitrogen. The mixture was then cooled and quenched with 2.4 ml of water, 2.4 ml of 15% sodium hydroxide solution and 7.5 ml of water. The inorganic salts were filtered and the filtrate evaporated. The residual oil was evaporatively distilled, bp 115° (5μ).

Anal. Calcd for C$_{17}$H$_{21}$N: C, 85.30; H, 8.84; N, 5.85. Found: C, 85.07; H, 8.94; N, 6.38.

NMR: multiplets from 120–200 cps (CH$_2$'s,13H); three broad peaks at 300, 310, 318 cps (=CH,2H); broad singlet at 344 cps (CH=CH$_2$, 3H); singlet 438 cps (5H).

EXAMPLE 4

N-Methyl-3a-phenyl-2,3,3a, 4,7,7a-cis-hexahydroisoindole

A. N-Methyl-1-phenyl-4-cyclohexene-1,2-dicarboximide

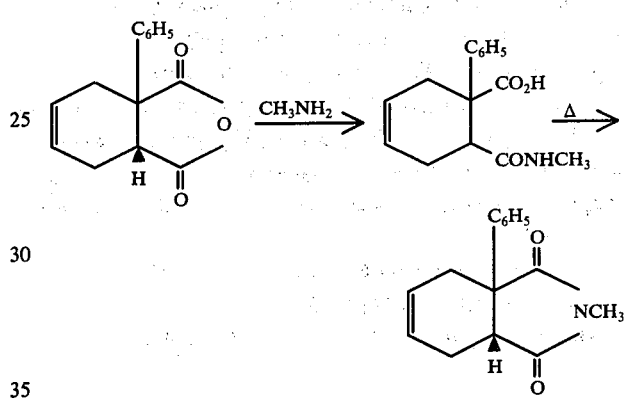

A solution of 1-phenyl-4-cyclohexene-1,2-dicarboxylic acid anhydride (11 g) and 300 ml of benzene was saturated with methylamine. The solution was refluxed for 1 hr., stirred at 25° for 18 hrs, then concentrated in vacuo and taken up in water. The aqueous layer was first extracted wih ether then acidified with 2N hydrochloric acid. The precipitated amidic acid was filtered and air dried to yield 8 g, mp 166°–167°.

The solid amidic acid was placed neat under nitrogen in a flask and heated at 190°–205° C for 1 hr. It was allowed to cool, taken up in ether, washed with aqueous sodium bicarbonate, then dried (anhydrous sodium sulfate) and evaporated to give an oil which crystallized on standing, mp 61.5°–62.5°.

IR: 5.55 and 5.80 μ (imide CO's); 6.0μ (C=C); 6.25; 6.28μ (Ar)

NMR: Multiplets from 130–190 cps (CH$_2$'s, 4H); singlet at 180 cps (NCH$_3$, 3H); AB quartet at 193, 195 and 201, 204 cps

1H; multiplet at 354–363 cps (=CH, 2H); singlet at 442 cps (ArH,5H).

Anal. Calcd for C$_{15}$ H$_{15}$NO$_2$: C, 74.67, H, 6.27; N, 5.81. Found: C, 74.06; H, 6.19 N, 5.80.

B. N-Methyl-3a-phenyl-2,3,3a4,7,7a-cis-hexahydroisoindole

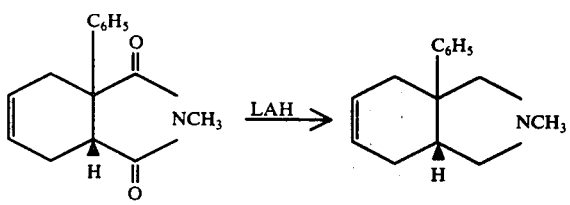

The product from Part A (3.7 g), lithium aluminum hydride (3.7 g) and 75 ml of anhydrous tetrahydrofuran were refluxed for 18 hrs, then cooled and treated with 3.7 ml of water, 3.7 ml of 15% sodium hydroxide solution, and finally 11.1 ml of water. The inorganic salts were filtered off and the filtrate evaporated. The resultant oil was evaporatively distilled, bp 70° (0.05 mm), yielding 2.6 g.

NMR: multiplets at 120-190 cps (CH$_2$'s,9H); singlet at 147 cps (NCH$_3$, 3H); broad singlet at 349 cps (=CH,2H); multiplet at 430-450 cps (5H).

IR: 6.0µ (C=C); 6.25, 6.30µ (Ar).

EXAMPLE 5

N-Methyl-3a-phenyl-cis-octahydroisoinodole

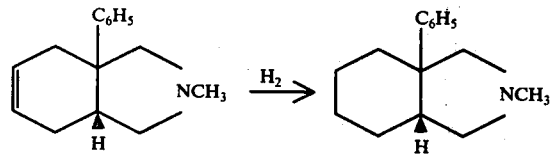

The product from Example 4 part B (1.78 g), 5% palladium on carbon (0.5 g) and 100 ml of ethanol were shaken, under 40 pounds per square inch (psi) of hydrogen, for 18 hrs at 25°. The reaction was filtered and the filtrate evaporated. The resulting oil was evaporatively distilled, by 90° (0.7 mm).

NMR: multiplet from 70-130 cps (CH$_2$'s,8H); singlet at 144 cps (NCH$_3$, 3H); multiplets from 153 to 183 cps (NCH$_2$'s and

5H); multiplet at 440 cps (5H).

EXAMPLE 6

N-Phenethyl-3a-(m-methoxyphenyl)-2,3,3a,4,7,7a-cis-hexahydroisoindole

A. Ethyl α-Hydroxymethylene-3-methoxyphenylacetate

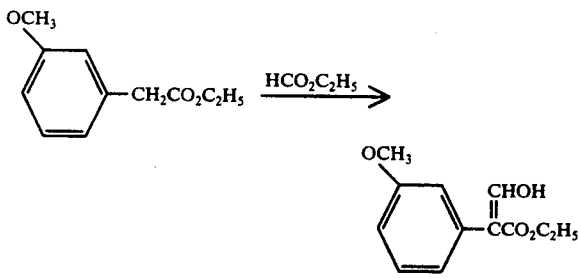

A mixture of sodium ethoxide in ether was prepared by adding 42.8 g of absolute ethanol in 200 ml of anhydrous ether to 40.8 g of a 55% suspension of sodium hydride in mineral oil and 350 ml of ether. After the addition was complete the mixture was cooled to −5° and a solution of 83.5 g of ethyl m-methoxyphenylacetate, 67.1 g of ethyl formate and 200 ml of ether was added keeping the temperature of the mixture at −5°. The reaction was then stirred 2 hours at 0° and finally for 18 hrs at 25°. It was poured into 2 liters of ice water and the aqueous layer separated, acidified with dilute sulfuric acid and extracted with ether to yield 88 g of product.

B. Ethyl-α-Cyanomethylene-3-methoxyphenylacetate

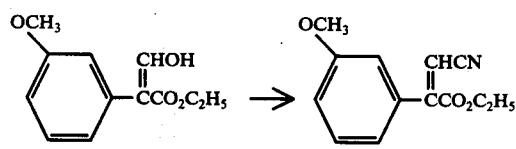

A mixture of 145 g of ethyl α-hydroxymethylene-3-methoxyphenylacetate, 300 g of hydrogen cyanide and 15 drops of aqueous potassium cyanide was stirred at 0° for 18 hrs. Concentrated sulfuric acid (20 drops) was added and the excess hydrogen cyanide evaporated. The crude residue was taken up in 750 ml of anhydrous pyridine and 125 ml of phosphorous oxychloride was added dropwise. The mixture was stirred for 18 hrs at 25° then concentrated, poured into dilute hydrochloric acid and extracted with ether. Distillation gave 100 g, bp 145° (1 mm). Gas chromatographic analysis and nmr spectra show the product consists of approximately equal amounts of the two possible isomers I and II,

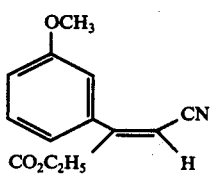 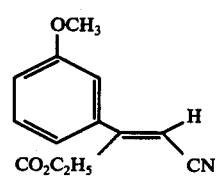

I            II

The nmr spectrum shows two vinyl proton resonances. Application of Matters et al. method (supra) of estimated chemical shifts for the vinyl protons of I and II gives values of 6.62δ (I) and 6.17δ (II) which can be compared with the observed values of 6.48δ and 5.93δ respectively This assignment is further confirmed by the hydrolysis of component II to form corresponding imide (via the amide and closure of the amide ester) (see part C below).

C. α-3-Methoxyphenyl-maleimide

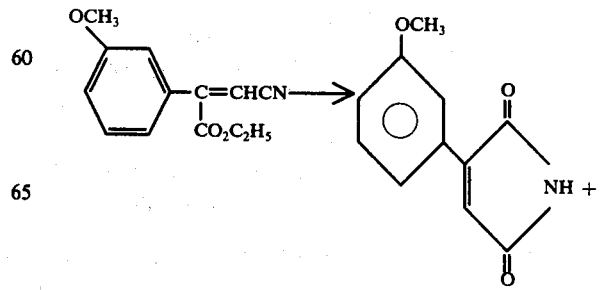

-continued

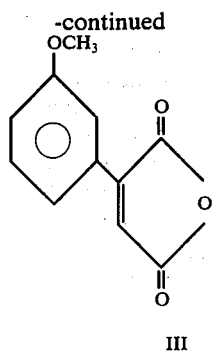

III

A mixture of 18.3 g of ethyl α-cyanomethylene-3-methoxyphenylacetate(consisting of two isomers I and II, see Part B above) and 100 ml of concentrated hydrochloric acid was refluxed for 2 hrs then poured into ice water and extracted with methylene chloride. After evaporation of the methylene chloride, the resulting residue was triturated with ether to give 6.5 g of a yellow solid, mp 122°–129°. Crystallization from acetonitrile gave some anhydride (III). Further evaporation of the solvent resulted in crystallization of the product imide, mp 134°–137°.

Distillation of the mother liquors resulting from the trituration with ether yields the pure isomer I, identified by the presence in the nmr of the vinyl proton resonance at 6.48δ (the vinyl proton resonance due to component V at 5.93δ was absent) and the presence of one peak in the gas chromatograph.

D. 1-(3-Methoxyphenyl)-4-cyclohexene-1,2-dicarboximide

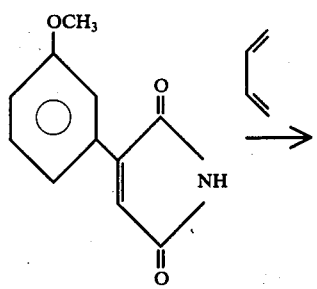

α-3-methoxyphenyl-maleimide (6.0 g), 75 ml of toluene and 25 ml of butadiene was heated at 100° for 15 hrs in a sealed bomb. The reaction was concentrated in vacuo then chromatographed on Florisil and eluted with acetone-hexane mixtures to yield a crude oil which was used in the next step without further purification.

E. N-Phenethyl-1-(m-methoxyphenyl-4-cyclohexene-1,2-dicarboximide

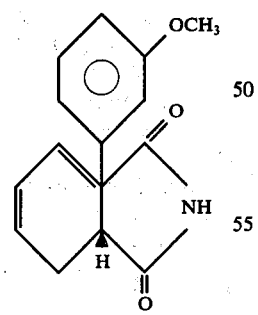

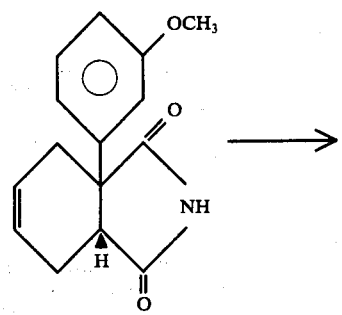

1-(m-Methoxyphenyl)-4-cyclohexene-1,2-dicarboximide (2 g) in 25 ml of anhydrous dimethylformamide was added to 0.4 g of 55% sodium hydride in mineral oil in 30 ml of dimethylformamide at 70° C. The mixture was heated at 70° for 1 hour after the distillation was complete, then cooled to 25°. Phenethyl bromide (1.8 g) in 10 ml of dimethylformamide was added the mixture heated at 80° for 18 hrs. The reaction was then poured into water and extracted with ether. The organic extracts were concentrated, evaporated and the residue evaporatively distilled, bp 225° (1μ). IR: 5.65, 5.9μ (imide C=O's).

F. N-Phenethyl-3a-(m-methoxyphenyl-2,3,3a4,7,7a-cis-hexahydroisoindole

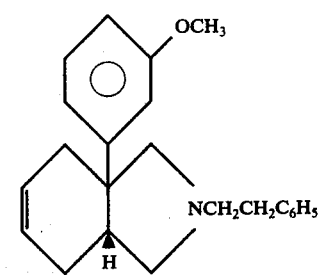

The product from Part E (1.8 g) was dissolved in 75 ml of anhydrous tetrahydrofuran and 1.8 g of lithium aluminum hydride added. The mixture was refluxed for 18 hrs then quenched with 1.8 ml of water, 1.8 ml of 15% aqueous sodium hydroxide and 5.4 ml of water. The inorganic salts were filtered and the filtrate evaporated. The resulting residue was evaporatively distilled, bp 210° (1μ).

Mass spectrum: Calcd for $C_{23}H_{27}NO$: 333.2091. Found: 333.2087.

EXAMPLE 7

N-Phenethyl-3a-(m-hydroxyphenyl)-2,3,3a,4,7,7a-cis-hexahydroisoindole

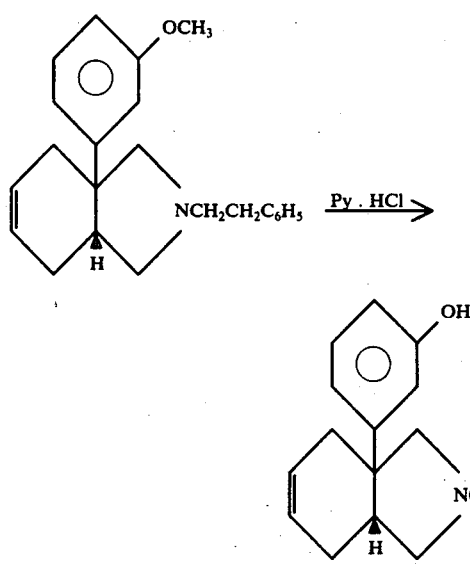

The product from Example 6 (1.4 g) was mixed with 7.0 g of anhydrous pyridine hydrochloride and the mixture heated at 210° for 1 hr after which time the reaction was cooled and diluted with water. It was basified with potassium carbonate and extracted with methylene chloride. After concentration of the extracts the residue was evaporatively distilled to yield 770 mg, bp 240° (1μ).

Mass spectrum: Calcd for $C_{22}H_{25}NO$: 319.1935. Found: 319.1930.

EXAMPLE 8

N-Phenethyl-3a-(m-hydroxyphenyl)-2,3,3a,4,7,7a-hexahydroisoindole Hydrochloride

The product from Example 7 was treated with an ether-hydrogen chloride mixture and the precipitate filtered to yield the hydrochloride salt, mp 115° (with decomposition)

EXAMPLE 9

N-Cyclopropylmethyl-3a-(m-methoxyphenyl)-2,3,3a,4,7,7 a-trans-hexahydroisoindole A. 4-(m-Methoxyphenyl)-4-carbethoxy-5-cyano-cyclohexene

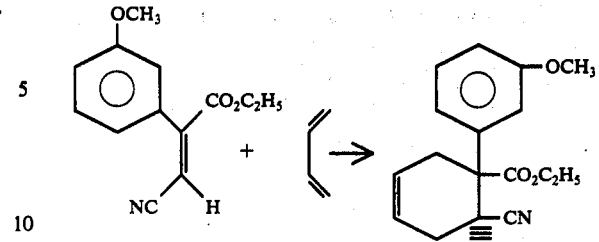

A mixture of 20 g of Product I (Example 6, part C), 100 ml of xylene, 25 mg of hydroquinone and 80 g butadiene was heated in a sealed tube at 200° for 15 hours. The mixture was concentrated then distilled through a short-path still to yield 12 g, bp 155° (0.05 mm).

B. 1-(m-Methoxyphenyl)-1(hydroxymethyl)-6-(aminomethyl)-2-cyclohexene

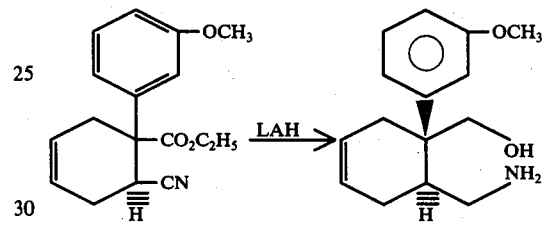

The product from Part A can be reacted with lithium aluminum hydride as in Example 1, Part C to yield 1-(m-methoxyphenyl)-1-(hydroxymethyl)-6-(aminomethyl)-2cyclohexene.

C. N-(p-Toluenesulfonyl)-3a-(m-methoxyphenyl)-2,3,3a,4,7,7a-trans-hexahydroisoindole

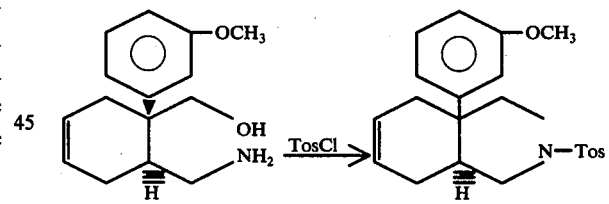

The product from Part B above can be reacted with triethylamine and p-toluenesulfonyl chloride in tetrahydrofuran as in Example 1, Part D to yield, after evaporative distillation, N-(p-toluenesulfonyl)-3a-(m-methodyphenyl)-2,3,3a,4,7,7a-trans-hexahydroisoindole.

D. 3a-(m-Methoxyphenyl)-2,3,3a,4,7,7a-trans-hexahydroisoindole

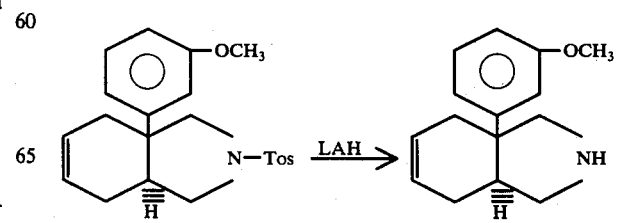

The product from Part C above can be reacted with lithium aluminum hydride as in Example 1, Part E to yield after evaporative distillation, 3a-(m-methoxyphenyl)-2,3,3a,4,7,7a-trans-hexahydroisoindole.

E. N-Cyclopropylcarbonyl-3a-(m-methoxyphenyl)-2,3,3a4,7,7a -trans-hexahydroisoindole

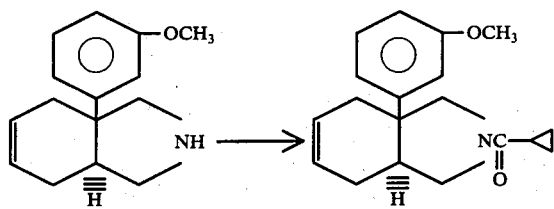

The product from Part D above can be reacted with cyclopropylcarbonyl chloride as shown in Example 1, Part F to yield N-cyclopropylcarbonyl-3a-(m-methoxyphenyl)-2,3,3a,4,7,6a-hexahydroisoindole.

Cyclobutylcarbonyl chloride can be used to give the corresponding N-cyclobutylcarbonyl-3a(m-methoxyphenyl)-2,3,3a,4,7,7a-hexahydroisoindole.

F. N-Cyclopropylmethyl-3a-(m-methoxyphenyl)-2,3,3a,4,7,7a-trans-hexahydroisoindole.

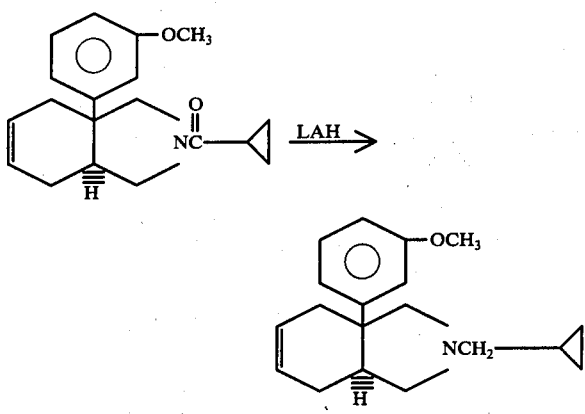

The product from Part E above can be reacted with lithium aluminum hydride as shown in Example 1, Part G to yield N-cyclopropylmethyl-3a-(m-methoxyphenyl)-2,3,3a,4,7,7a-trans-hexahydroisoindole.

The corresponding cyclobutyl carbonyl compound from Part E can give under these reaction conditions, N-cyclobutylmethyl-3a-(m-methoxyphenyl)-2,3,3a,4,7,-7a-trans-hexahydroisoindole.

EXAMPLE 10
N-Cyclopropylmethyl-3a-(m-hydroxyphenyl)-2,3,3a,4,7,7a-trans-hexahydroisoindole

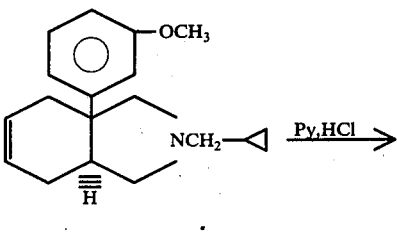

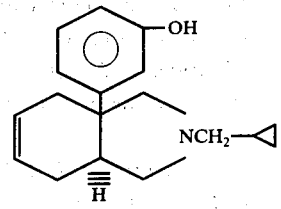

The product from Example 9, Part F, and pyridine hydrochloride can be heated under nitrogen at 200° for 1 hour and the reaction worked up as in Example 2 to yield, after evaporative distillation, the above product.

EXAMPLE 11
N-Cyclobutylmethyl-3a-(m-hydroxxyphenyl)-2,3,3a,4,7,7a-trans-hexahydroisoindole

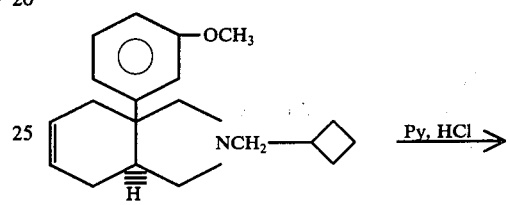

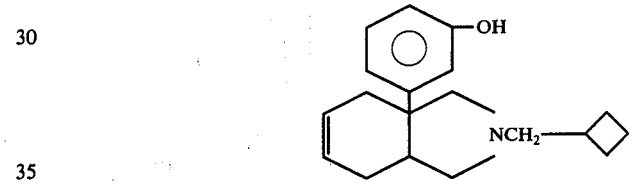

The alternate product from Example 9, Part F, can be reacted with pyridine hydrochloride at 190° to yield, after evaporative distillation, the product named above.

Using the procedures disclosed, additional compounds of the invention can be prepared as for example, N-(p-methylphenethyl)-3a-(m-hydroxyphenyl)-octahydroisoindole; N-(m-isobutylbenzyl)-3a-(m-hydroxyphenyl)-octahydroisoindolone; N-cyclopropyklmethyl-3a-(m-hydroxyphenyl)-octahydrroisoindole; N-(3,3-dimethylallyl)-3a-(m-hydroxyphenyl)-octahydroisoindole; N-(p-dimethylaminophenethyl)-3a-(m-hydroxyphenyl)-octahydroisoindole; and N-(cyclobutylmethyl)-3a-(m-hydroxyphenyl)-octahydroisoindole.

These are obtained by alkylation with appropriate halogenated alkylating reagents (e.g., p-methylphenethyl chloride and 3,3-dimethylallylchloride) of 3 a(m-methoxyphenyl)-2,3,3a,4,7,7a,-hexahydroisoindole (which in turn is prepared using butadiene instead of dimethylbutadiene as in Example 1) followed by replacement of the methoxy by hydroxy as in Example 2.

Dosage Forms and Use

The compounds of the invention can be administered by any means that produces contact of the active agent with the compounds's site of action in the body of a mammal. They can be administered by any conventional means available for use in conjunction with pharmaceuticals, either as individual therapeutic agents or in a combination of therapeutic agents. They can be administered alone, but are generally administered with a suitable non-toxic pharmaceutical carrier selected on the basis of the chosen route of administration and standard pharmaceutical practice.

The dosage administered will, of course, vary depending upon known factors such as the pharmcodynamic characteristics of the particular agent, and its mode and route of administration; age, health, and weight of the recipient; nature and extent of symptons, kind of concurrent treatment, frequency of treatment, and the effect desired. Usually a daily dosage of active ingredient can be about 0.01 to 100 milligrams per kilogram of body weight. Ordinarily a dosage of about 0.1 to 50, preferably about 1 to 25 milligrams, per kilogram per day given in divided doses 2 to 4 times a day or in sustained release form is effective to obtain desired results.

Dosage forms (compositions) suitable for internal administration can contain from about 25 milligrams to about 75 milligrams of active ingredient per unit. In these pharmaceutical compositions the active ingredient will ordinarily be present in an amount of about 0.5–95% by weight based on the total weight of the composition.

The active ingredient can be administered orally in solid dosgae forms, such as capsules, tablets, and powders, or in liquid dosage forms, such as elixers, syrups, and suspensions; it can also be administered parenterally, in sterile liquid dosage forms; or rectally in the form of suppositories.

Gelatin capsules can contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmoshere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium ethylene diamine triamine (EDTA). In addition, parenteral solutions can contain preservatives, such as benzalkonium chloride, methyl- or propylparaben, and chlorobutanol.

Suppositories can contain the active ingredient in a suitable oleaginous or water-soluble base. The oleaginous class includes cocoa butter and fats with similar properties; the water-soluble class includes polyethylene glycols.

Suitable pharmaceutical carriers are described in Remington's Pharmaceutical Sciences, E.W. Martin, a standardreference text in this field.

Useful pharmaceutical dosage-forms for administration of the compounds of this invention can be illustrated as follows:

CAPSULES

A large number of unit capsules are prepared by filling standard two-piece hard gelatin capsules each with 50 milligrams of powdered active ingredient, 110 milligrams of lactose, 32 milligrams of talc, and 8 milligrams magnesium stearate.

CAPSULES

A mixture of active ingredient in soybean oil is prepared and injected by means of a positive displacement pump into gelatin to form soft gelatin capsules containing 50 milligrams of the active ingredient. The capsules are washed in petroleum ether and dried.

TABLETS

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by filtration.

SUSPENSION

An aqueous suspension is prepared for oral administration so that each 5 milliliters contain 10 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

INJECTABLE

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

EXAMPLE A

A standard procedure for detecting and comparing the analgesic acitivity of the compounds, for which there is good correlation with human efficacy, is the standard phenylquinone writhing (PQW) test modified from Siegmund, et al., *Proc. Soc. Exp. Biol. Med.* 95, 729 (1957). A test compound suspended in 1% methylcellulose was given orally to fasted (17–21 hours) femal white mice, 5–20 animals per double blind test. Aqueous (0.01% phenyl-p-benzoquinone)phenylquinone was injected intraperitoneally at 23 or 30 minutes later using 0.25 ml per mouse. Commencing at 30 or 37 minutes, respectively, after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Weil, *Biomtrics* 8, 249 (1952).

Table I below shows the oral $ED_{50}$ dosages (in mg/kg of body weight) of a number of compounds of the invention. Ideally a low $ED_{50}$ dosage for PQW and a high ED$_{50}$ dosage for PQW and a high ED$_{50}$ dosage for ST (Straub Tail) is desired.

Table I

| Compound of Example | Structure | PQW ED$_{50}$ | ST ED$_{\%0}$ |
|---|---|---|---|
| 1. | ![structure with OCH$_3$, CH$_3$, CH$_3$, NCH$_2$-cyclopropyl, H] | 78 | >135 |
| 2. | ![structure with OH, CH$_3$, CH$_3$, NCH$_2$-cyclopropyl, H] | 120 | >162 |
| 3. | ![structure with NCH$_2$CH=CH$_2$, H] | 140 | >200 |
| 4. | ![structure with C$_6$H$_5$, NCH$_3$, H] | 32 | >162 |
| 5. | ![structure with C$_6$H$_5$, NCH$_3$, H] | 90 | >200 |
| 6. | ![structure with OCH$_3$, NCH$_2$CH$_2$C$_6$H$_5$, H] | 26 | — |
| 7. | ![structure with OH, NCH$_2$CH$_2$C$_6$H$_5$, H] | 19 | — |
| 8. | ![structure with OH, N—CH$_2$CH$_2$C$_6$H$_5$ . HCl] | 19 | — |

There is a close correlation between a drug's addiction liability and its ability to cause Straub tail in mice [Shemano and Wendel, Tox. Appl. Pharm., 6, 334–339 (1964)] at doses much below the LD$_{50}$. Known narcotic antagonists such as naloxone, nalorphine, and pentazocine can prevent the induction of Straub tail in mice by a highly addicting agonist such as morphine [Blumberg, Dayton, and Wolf, The Pharmacologist, 10(2), 189 (1968)]. This property is the basis of a test for detecting new narcotic antagonist drugs.

EXAMPLE B

17–21 Hour fasted female CF$_1$S mice 5 per dose were injected subcutaneously (loose skin inside hind limb) with test drug at 0.67, 2, 6, 18, 54, and 162 mg/kg in 0.20 ml 1% Methocel per mouse. 10 Minutes later, a dosage of 40 mg/kg (base weight) of morphine sulfate in 0.20 ml 1% Methocel per mouse was given subcutaneously (nape of neck). The mice were observed continuously for the next 20 minutes after the first mouse of a group of 30 had received morphine. Prevention of a 90° Straub tail during this observation period was taken as indica-tion of narcotic antagonist ability. The table below gives the results for several compounds.

| Compound of Example | ED$_{50}$ (mg/kg) |
|---|---|
| 2 | 5.2 |
| 7 | 43 |
| 8 | 54 |
| Pentazocine (a known narcotic antagonist) | 4 |
| | 4 |

I claim:

1. A compound of the group (A) having the general formula

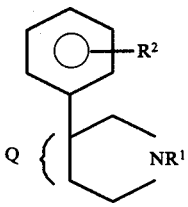

wherein
R$^1$ is H, alkyl of 1–8 carbons,
—CH$_2$Y where Y is alkenyl or alkynyl of 2–6 carbons,

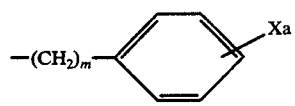

where $m$ is 1 or 2, $a$ is 0 or 1 and X is F, Cl, Br, CF$_3$, OCH$_3$, CH$_3$, C$_2$H$_5$, C$_3$H$_7$, C$_4$H$_9$ —NH$_2$ or N(CH$_3$)$_2$,

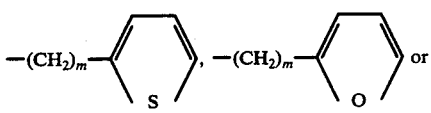

where $m$ is 1 or 2 and $n$ is 2–5.
R$^2$ is H, OH, OCH$_3$, F, or OCOR$^3$ where R$^3$ is alkyl or 1–3 carbons; and
Q is:

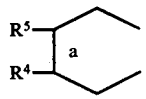

(1)

in which
R$^4$ and R$^5$ are each H or CH$_3$, or
R$^4$ and R$^5$ are H, CH$_3$, C$_2$H$_5$, $i$—C$_3$H$_7$, Cl, or OCH$_3$ with the proviso that one only of R$^4$ or R$^5$ is hydrogen;
$a$ is a single or double bond; with the proviso that when R$^4$ or R$^5$ is Cl or OCH$_3$, $a$ is a double bond; or

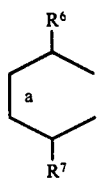 (2)

in which
R$^6$ and R$^7$ are each OH or OCOCH$_3$; or
R$^6$ and R$^7$ are H, OH, OCOCH$_3$, OCH$_3$ or CH$_3$ with the proviso that one only of R$^6$ or R$^7$ is H;
a is a single or double bond; and
(B) a pharmaceutically acceptable acid addition salt of (A).

2. A compound of claim 1 which is (A).
3. A compound of claim 1 which is (B).
4. A compound of claim 1 which is in the cis-form.
5. A compound of claim 1 which is in the trans-form.
6. A compound of claim 1 where R$^1$ is hydrogen.
7. A compound of claim 1 where R$^1$ is alkyl of 1-8 carbons.
8. A compound of claim 1 where R$^1$

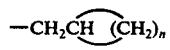

where $n=2-5$.

9. A compound of claim 1 where R$^1$ is cyclopropylmethyl.
10. A compound of claim 1 where R$^2$ is H.
11. A compound of claim 1 where R$^2$ is OH.
12. A compound of claim 1 where R$^2$ is OCH$_3$.
13. The compound of claim 1 which is N-cyclopropylmethyl-3a-(m-methoxyphenyl)-5,6-dimethyl-2,3,3a,4,7,7a-trans-hexahydroisoindole.
14. The compound of claim 1 which is N-cyclopropylmethyl-3a-(m-hydroxyphenyl)-5,6-dimethyl-2,3,3a,4,7,7a-trans-hexahydroisoindole.
15. The compound of claim 1 which is N-allyl-3a-phenyl-2,3,3a,4,7,7a-cis-hexahydroisoindole.
16. The compound of claim 1 which is N-methyl-3a-phenyl2,3,3a,4,7,7a-cis-hexahydroisoindole.
17. The compound of claim 1 which is N-methyl-3a-phenyl-cis-octahydroisoindole.
18. The compound of claim 1 which is N-phenethyl-3a-(m-methoxyphenyl)-2,3,3a,4,7,7a-cis-hexahydroisoindole.
19. The compound of claim 1 which is N-phenyethyl-3a-(m-hydroxyphenyl)-2,3,3a,4,7,7a-cis-hexahydroisoindole.
20. The compound of claim 1 which is N-phenyethyl-3a-(m-hydroxyphenyl)-2,3,3a,4,7,7a-cis-hexahydroisoindole hydrochloride.
21. A pharmaceutical composition comprising a suitable pharmaceutical carrier and an effective analgesic amount of a compound of claim 1.
22. A pharmaceutical composition comprising a suitable pharmaceutical carrier and an effective analgesic amount of a compound of claim 2.
23. A pharmaceutical composition comprising a suitable pharmaceutical carrier and an effective analgesic amount of a compound of claim 3.
24. A pharmaceutical composition comprising a suitable pharmaceutical carrier and an effective analgesic amount of a compound of claim 4.
25. A pharmaceutical composition comprising a suitable pharmaceutical carrier and an effective analgesic amount of a compound of claim 5.
26. A pharmaceutical composition comprising a suitable pharmaceutical carrier and an effective analgesic amount of a compound of claim 6.
27. A pharmaceutical composition comprising a suitable pharmaceutical carrier and an effective analgesic amount of a compound of claim 7.
28. A pharmaceutical composition comprising a suitable pharmaceutical carrier and an effective analgesic amount of a compound of claim 8.
29. A pharmaceutical composition comprising a suitable pharmaceutical carrier and an effective analgesic amount of a compound of claim 9.
30. A pharmaceutical composition comprising a suitable pharmaceutical carrier and an effective analgesic amount of a compound of claim 10.
31. A pharamaceutical composition comprising a suitable pharmaceutical carrier and an effective analgesic amount of a compound of claim 11.
32. A pharmaceutical composition comprising a suitable pharmaceutical carrier and an effective analgesic amount of a compound of claim 12.
33. A pharmaceutical composition comprising a suitable pharmaceutical carrier and an effective analgesic amount of a compound of claim 13.
34. A pharmaceutical composition comprising a suitable pharmaceutical carrier and an effective analgesic amount of a compound of claim 14.
35. A pharmaceutical composition comprising a suitable pharmaceutical carrier and an effective analgesic amount of a compound of claim 15.
36. A pharmaceutical composition comprising a suitable pharmaceutical carrier and an effective analgesic amount of a compound of claim 16.
37. A pharmaceutical composition comprising a suitable pharmaceutical carrier and an effective analgesic amount of a compound of claim 17.
38. A pharmaceutical composition comprising a suitable pharmaceutical carrier and an effective analgesic amount of a compound of claim 18.
39. A pharmaceutical composition comprising a suitable pharmaceutical carrier and an effective analgesic amount of a compound of claim 19.
40. A pharmaceutical composition comprising a suitable pharmaceutical carrier and an effective analgesic amount of a compound of claim 20.
41. A method of producing analgesia in a mammal which comprises administering to the mammal an effective analgesic amount of a compound of claim 1.
42. A method of producing analgesia in a mammal which comprises administering to the mammal an effective analgesic amount of a compound of claim 2.
43. A method of producing analgesia in a mammal which comprises administering to the mammal an effective analgesic amount of a compound of claim 3.
44. A method of producing analgesia in a mammal which comprises administering to the mammal an effective analgesic amount of a compound of claim 4.
45. A method of producing analgesia in a mammal which comprises administering to the mammal an effective analgesic amount of a compound of claim 5.
46. A method of producing analgesia in a mammal which comprises administering to the mammal an effective analgesic amount of a compound of claim 6.

47. A method of producing analgesia in a mammal which comprises administering to the mammal an effective analgesic amount of a compound of claim 7.

48. A method of producing analgesia in a mammal which comprises administering to the mammal an effective analgesic amount of a compound of claim 8.

49. A method of producing analgesia in a mammal which comprises administering to the mammal an effective analgesic amount of a compound of claim 9.

50. A method of producing analgesia in a mammal which comprises administering to the mammal an effective analgesic amount of a compound of claim 10.

51. A method of producing analgesia in a mammal which comprises administering to the mammal an effective analgesic amount of a compound of claim 11.

52. A method of producing analgesia in a mammal which comprises administering to the mammal an effective analgesic amount of a compound of claim 12.

53. A method of producing analgesia in a mammal which comprises administering to the mammal an effective analgesic amount of a compound of claim 13.

54. A method of producing analgesia in a mammal which comprises administering to the mammal an effective analgesic amount of a compound of claim 14.

55. A method of producing analgesia in a mammal which comprises administering to the mammal an effective analgesic amount of a compound of claim 15.

56. A method of producing analgesia in a mammal which comprises administering to the mammal an effective analgesic amount of a compound of claim 16.

57. A method of producing analgesia in a mammal which comprises administering to the mammal an effective analgesic amount of a compound of claim 17.

58. A method of producing analgesia in a mammal which comprises administering to the mammal an effective analgesic amount of a compound of claim 18.

59. A method of producing analgesia in a mammal which comprises administering to the mammal an effective analgesic amount of a compound of claim 19.

60. A method of producing analgesia in a mammal which comprises administering to the mammal an effective analgesic amount of a compound of claim 20.

61. A method of producing narcotic antagonism in a mammal which comprises administering to the mammal an effective narcotic antagonist amount of a compound of claim 14.

62. A method of producing narcotic antagonism in a mammal which comprises administering to the mammal an effective narcotic antagonist amount of a compound of claim 19.

63. A method of producing narcotic antagonism in a mammal which comprises administering to the mammal an effective narcotic antagonist amount of a compound of claim 20.

* * * * *